United States Patent [19]

White

[11] Patent Number: 4,730,059

[45] Date of Patent: * Mar. 8, 1988

[54] 6'-THIOMETHYLSUBSTITUTED SPECTINOMYCINS

[75] Inventor: David R. White, Kalamazoo, Mich.

[73] Assignee: The Upjohn Company, Kalamazoo, Mich.

[*] Notice: The portion of the term of this patent subsequent to Jul. 29, 2003 has been disclaimed.

[21] Appl. No.: 838,317

[22] Filed: Mar. 10, 1986

[51] Int. Cl.$^4$ .................. C07D 323/04; C07D 493/00
[52] U.S. Cl. .................................... 549/361; 549/214
[58] Field of Search ................................ 549/361, 214

[56] References Cited

U.S. PATENT DOCUMENTS

| | | |
|---|---|---|
| 3,234,092 | 2/1966 | Bergy et al. |
| 4,345,086 | 8/1982 | White ................................ 549/16 |
| 4,351,771 | 9/1982 | White et al. ........................ 549/361 |
| 4,380,651 | 4/1983 | White ................................ 549/361 |
| 4,380,652 | 4/1983 | White ................................ 549/361 |
| 4,405,797 | 9/1983 | Thomas .............................. 549/361 |
| 4,420,623 | 12/1983 | White .............................. 549/361 |
| 4,465,848 | 4/1984 | Thomas et al. ..................... 549/361 |
| 4,532,336 | 7/1985 | White ................................ 549/361 |
| 4,578,485 | 3/1986 | White ................................ 549/361 |
| 4,603,212 | 7/1986 | White ................................ 549/361 |

FOREIGN PATENT DOCUMENTS 2117757A 10/1983 United Kingdom ................ 549/361

OTHER PUBLICATIONS

J. Am. Chem. Soc., "Synthesis of (+)-Spectinomycin", Stephen Hanessian, 101, 5839–5841, (1979).

Primary Examiner—Nicky Chan
Attorney, Agent, or Firm—Bruce Stein

[57] ABSTRACT

Disclosed are 6'-thiomethylsubstituted spectinomycins (XII) which are useful in the same way as other spectinomycin pharmaceutical agents.

6'-Thiomethylsubstituted (XIV) and protected spectinomycin (XIII) intermediates useful in the production of 6'-thiomethylsubstituted spectinomycins (XII) and 6'-alkenylspectinomycins (IX) are also disclosed.

9 Claims, No Drawings

6'-THIOMETHYLSUBSTITUTED SPECTINOMYCINS

BACKGROUND OF THE INVENTION

Spectinomycin is a known antibiotic and was first prepared by a microbiological process, see U.S. Pat. No. 3,234,092. Since that time spectinomycin has been synthesized chemically, see J. Am Chem. Soc. 101, 19 (1979) and U.S. Pat. No. 4,351,771.

6'-Methylspectinomycin analogs and intermediates useful in production of 6'-methylspectinomycin are known, see U.S. Pat. Nos. 4,380,651 and 4,380,652.

U.S. Pat. No. 4,465,848 discloses a process for demethylation of spectinomycin and its analogs and realkylation of the intermediates. U.S. Pat. No. 4,532,336 discloses 6'-alkylspectinomycins and intermediates useful in preparation thereof.

U.S. Pat. No. 4,351,771 claims 6'-alkenylspectinomycins.

The present invention involves 6'-thiomethyl-substituted spectinomycins (XII) pharmacologically active end products and intermediates enamine (V), 6'-methylidene substituted spectinomycins (VI), triprotected 6'-alkenyl-4',5'-didehydrospectinomycins (VII), amine protected 6'-alkenylspectinomycins (VIII), triprotected 6'-thiomethyl-substituted spectinomycins (X) and amine protected 6'-thiomethyl-substituted spectinomycins (XI) intermediates.

SUMMARY OF THE INVENTION

Disclosed is a pharmacologically useful 6'-thiomethyl-substituted spectinomycin (XII).

Further disclosed are protected spectinomycins (XIII) and 6'-thiomethyl-substituted (XIV) intermediates.

DETAILED DESCRIPTION OF THE INVENTION

The two biologically active spectinomycin end products, 6'-alkenylspectinomycin (IX) and 6'-thiomethyl-substituted spectinomycin (XII) are both produced from a novel common intermediate, 6'-methylidene substituted spectinomycin (VI). The 6'-methylidene substituted spectinomycin (VI) is produced from spectinomycin following the general procedure of U.S. Pat. No. 4,532,336. The amino protecting groups of U.S. Pat. No. 4,532,336 can not be readily removed without interference from the 6'-thio substituent whereas the amino protecting groups used in the present invention can be removed without interference from the 6'-thio substituent.

The spectinomycin starting materials are well known those skilled in the art, see The Merck Index, Tenth Edition, 1983, Monograph 8584. First, the free amine groups of the spectinomycin must be protected with certain amine protecting groups which are removable in the presence of C-6'-unsaturation or thioether substitution. Suitable amine blocking groups include those of $R_1$, and equivalents thereof as is well known to those skilled in the art, see Protective Groups in Organic Synthesis by T. W. Greene, Wiley, 1981. It is preferred that $R_1$ be t-butoxy-carbonyl (t-BOC). The preparation of amine protected spectinomycin (I) from spectinomycin where $R_1$ is t-BOC is described in U.S. Pat. No. 4,465,848.

The amine protected spectinomycin (I) is converted to the corresponding hydroxy/amine protected spectinomycin (II) by methods well known to those skilled in the art, see Greene, supra, and U.S. Pat. No. 4,532,336. The amine protected spectinomycin (I) is reacted with formic acid in the presence of a carboxylic acid anhydride and a base in a suitable solvent such as THF or ethyl acetate. It is preferred that the base is pyridine.

The hydroxy/amine protected spectinomycin (II) is then further acylated under more vigorous conditions such as heating, increased time of reaction, etc and using a catalyst such as dimethylamino pyridine to produce the corresponding acylated spectinomycin (III) by methods well known to those skilled in the art, see Greene, supra, and U.S. Pat. No. 4,532,336. It is preferred that the acylating agent be an anhydride and it is preferred that the anhydride be acetic anhydride. It is preferred that $R_3$ be a methyl group.

The acylated spectinomycin (III) is converted to the corresponding $\alpha,\beta$-unsaturated ketone (IV) by methods well known to those skilled in the art, see U.S. Pat. No. 4,532,336.

The $\alpha,\beta$-unsaturated ketone (IV) is converted to the corresponding enamine (V) by methods well known to those skilled in the art, see U.S. Pat. No. 4,532,336. It is preferred that $R_4$ and $R_5$ are methyl groups.

The enamine (V) is converted to the corresponding 6'-methylidene substituted spectinomycin (VI) by methods well known to those skilled in the art, see U.S. Pat. No. 4,532,336.

The 6'-methylidene substituted spectinomycin (VI) intermediate can be converted to either the 6'-alkenyl-spectinomycin (IX) by reaction with the appropriate Grignard reagent and subsequent deblocking or it can be converted to the 6'-thiomethyl-substituted spectinomycin (XII) by reaction with the appropriate thiol and subsequent deblocking.

The 6'-methylidene substituted spectinomycin (VI) is converted to the corresponding hydroxy/amine protected 6'-alkenyl-4',5'-didehydrospectinomycin (VII) by methods well known to those skilled in the art, see U.S. Pat. No. 4,532,336. In the side chain of the hydroxy/amine protected 6'-alkenyl-4',5'-didehydrospectinomycin (VII) a is 0 thru 4; preferably a is 0. When a is 0 the side chain is $—CH_2CH_2—C(R_8)=C(R_9)(R_{10})$. It is preferred that $R_8$, $R_9$ and $R_{10}$ are —H. The triprotected-6'-alkenyl-4',5'-didehydrospectinomycin (VII) is converted to the corresponding amine protected 6'-alkenyl-spectinomycin (VIII) by reducing and deprotecting conditions well known to those skilled in the art, see Greene, supra, and U.S. Pat. No. 4,532,366.

The amine protected 6'-alkenylspectinomycin (VIII) is converted to the corresponding 6'-alkenylspectinomycin (IX) by methods well known to those skilled in the art, see Greene, supra.

With the hydroxy/amine protected 6'-alkenyl-4',5'-didehydrospectinomycin (VII), amine protected 6'-alkenylspectinomycin (VIII) and 6'-alkenylspectinomycin (IX) the side chain can give either cis or trans configuration and both are meant to be included by the formulas (VII, VIII and IX).

The 6'-methylidene substituted spectinomycin (VI) is converted to the corresponding hydroxy/amine protected 6'-thiomethyl-substituted spectinomycin (X) by methods well known to those skilled in the art. The addition or mercaptans to activated olefins is well known, see R. B. Wagner and H. D. Zook, Synthetic Organic Chemistry, Wiley, p. 788. Further discussion of the Michael addition is found in Modern Synthetic Reaction by H. O. House, W. A. Benjamin, 1972, beginning on p 595.

The triprotected 6'-thiomethyl-substituted spectinomycin (X) is converted to the corresponding amine protected 6'-thiomethyl-substituted spectinomycin (XI) by methods well known to those skilled in the art, see Greene, supra, and U.S. Pat. No. 4,532,336.

The amine protected 6'-thiomethyl-substituted spectinomycin (XI) is converted to the corresponding 6'-thiomethyl-substituted spectinomycin (XII) by methods well known to those skilled in the art, see Greene, supra, and U.S. Pat. No. 4,532,336. It is preferred that $R_{11}$ is $C_1$-$C_3$ alkyl.

With the amine protected 6'-alkenylspectinomycin (VIII), 6'-alkenylspectinomycin (IX), 6'-thiomethyl-substituted spectinomycin (XI) and 6'-thiomethyl-substituted spectinomycin (XII), the side chain is in the "α" position. For the compounds of formulas (XII and XIV), when the ---- is a single bond the side chain is in the α configuration.

The 6'-alkenylspectinomycins (IX) and 6'-thiomethyl-substituted spectinomycins (XII) and pharmaceutically acceptable salts thereof are useful antibacterial agents and are generally used in the same manner and same way as other spectinomycin pharmaceutical agents are used, see for example, U.S. Pat. Nos. 3,234,092 (spectinomycin), 4,532,336 (6'-alkylspectinomycin).

The 6'-alkenylspectinomycin (IX) and 6'-thiomethyl-substituted spectinomycins (XII) are used in a dosage range of about 1 to about 200 mg/kg/day, preferably from about 20 to about 60 mg/kg/day, more preferably administered from 1 thru 4 tims a day, preferably one or twice a day, more preferably once a day. Treatment may last 1–14 days, preferably 1 or 2 days.

The exact dosage and frequency of administration depends on the particular condition being treated, the severity of the condition being treated, the age, weight, general physical condition of the patient and other medication the individual may be taking as is well known to those skilled in the art and can be more accurately determined by measuring the concentration of the 6'-alkenylspectinomycin (IX) or 6'-thiomethyl-substituted spectinomycin (XII) in the patient's blood.

DEFINITIONS

The definitions and explanations below are for the terms as used throughout the entire patent application including both the specification and the claims.

All temperatures are in degrees Centigrade.

TLC refers to thin-layer chromatography.

t-BOC refers to t-butyloxycarbonyl which is $(CH_3)_3C—O—CO—$.

THF refers to tetrahydrofuran.

DMF refers to dimethylformamide.

SSB refers to an isomeric mixture of hexanes.

Saline refers to an aqueous saturated sodium chloride solution.

UV refers to ultraviolet spectroscopy.

CMR refers to C-13 magnetic resonance spectroscopy, chemical shifts are reported in ppm (δ) downfield from TMS.

TMS refers to tetramethylsilane.

4-DMAP refers to 4-(dimethylamino)pyridine.

MS refers to mass spectrometry expressed as m/e or mass/change unit. $[M+H]^+$ refers to the positive ion of a parent plus a hydrogen atom.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

----- is a single or double bond with the proviso that
(1) when ⋯ is a double bond
  (a) $R_{12}$ is $R_3$—CO—
(2) when ---- is a single bond
  (b) $R_{12}$ is a hydrogen atom and
  (c) R is —CH$_2$CH$_2$—[C(R$_6$)(R$_7$)]$_a$—C(R$_8$)=C(R$_9$)(R$_{10}$)

When the term "$C_x$-$C_y$ alkyl" or "Cx-Cy alkyl" is used, it means alkyl of x thru y carbon atoms inclusive and includes isomers threof where such exist.

When the term "$C_x$-$C_y$ cycloalkyl" or "Cx-Cy cycloalkyl" is used, it means cycloalkyl or x thru y carbon atoms inclusive.

When the term "$C_x$-$C_y$ atoms" or "Cs-Cy atoms" is used, it means x thru y total atoms inclusive whether carbon, nitrogen, oxygen, sulfur or other type of atom.

R is trans—CH=CH—N(R$_4$)(R$_5$), —CH=CH$_2$, —CH$_2$CH$_2$—[C(R$_6$)(R$_7$)]$_a$—C(R$_8$)=C(R$_9$)(R$_{10}$) with the proviso that when a >0, only one of the R$_6$'s or R$_7$'s can be isopropyl.

$R_1$ is —COO—(t-butyl), —COO—CH$_2$CH$_2$Si(CH$_3$)$_3$ or —COO—CH$_2$CH$_2$Cl;

$R_3$ is $C_1$-$C_8$ alkyl;

$R_4$ is $C_1$-$C_8$ alkyl or $C_5$-$C_8$ cycloalkyl;

$R_5$ is $C_1$-$C_8$ alkyl or $C_5$-$C_8$ cycloalkyl;

$R_6$ is —H or $C_1$-$C_3$ alkyl;

$R_7$ is —H or $C_1$-$C_3$ alkyl;

$R_8$ is —H or $C_1$-$C_5$ alkyl, or $R_8$ and $R_9$ taken together with the olefinic double bond to which $R_8$ and $R_9$ are joined form a cycloalkene group $C_4$-$C_7$;

$R_9$ and $R_{10}$ are each —H or $C_1$-$C_5$ alkyl, or $R_9$ and $R_{10}$ taken together with the carbon atom to which they are attached form a cycloalky group of $C_5$-$C_7$;

$R_{11}$ is $C_1$-$C_5$ alkyl, —CH$_2$—(C$_2$-C$_4$ alkenyl), $C_5$-$C_8$ cycloalkyl, phenyl or phenyl substituted with 1 thru 5, —F, —Cl, —Br, or —I and when $R_{11}$ is phenyl substituted with 1 thru 5 halogen atoms, the halogen atoms must be the same;

$R_{12}$ is —H or $R_3$—CO— with the proviso that when $R_{12}$ is —H, the ---- is a single bond and when $R_{12}$ is $R_3$—CO—, ---- is a double bond;

a is 0 thru 4.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

N,N'-Di-t-butoxycarbonyl-2,6-bis(O-formyl)-spectinomycin (II)

Acetic anhydride (465 ml) followed by pyridine (720 ml) is slowly added to a mixture of formic acid (190 ml) in ethylacetate (960 ml) cooled to −78° under nitrogen. N,N'-d-t-butoxycarbonylspectinomycin (I, U.S. Pat. No. 4,465,848 Example 3, 67 g) is added quickly and the mixture is allowed to warm to 20°–25°. After 12 hr, TLC probe (methanol/chloroform, 5/95) shows the starting material has been converted to a less polar product. The reaction mixture is diluted with ethyl acetate (1 l) and extracted with aqueous potassium bisulfate (10% w/v) until the wash pH is less than 3. The organic mixture is washed with saturated sodium bicarbonate (1 l), water (1 l) and saline (1 l), dried over magnesium sulfate and concentrated to give the title compound, CMR (CD$_3$COCD$_3$) 97.3, 91.9, 79.6, 75.2, 74.4, 68.1, 66.4, 65.7, 60.3, 57.4, 45.6, 30.8, 28.6, 21.6 δ; MS [M+H]+ 561, 433, 405, 389, 361, 225, 197, 140, 122, 89, 57, 45.

EXAMPLE 2

N,N'-Di-t-BOC-2,6-bis(O-formyl)-2'-acetylspectinomycin-3'-enolacetate (III)

To a mixture of N,N'-di-t-BOC-2,6-bis(O-formyl)-spectinomycin, (II, Example 1, 72.2 g) in ethyl acetate (600 ml) is added acetic anhydride (235 ml), pyridine (350 ml) and 4-DMAP (5.60 g). The mixture is heated for 17 hours at 55° under a nitrogen atmosphere. TLC (ethylacetate/chloroform, 3/7) shows a slightly less polar spot with no residual starting material. The solution is diluted with ethyl acetate (500 ml) and n-hexane (500 ml) and extracted with saturated potassium bisulfate until the wash pH is less than 3. The organic solution is then washed with saturated sodium bicarbonate. (1 l), water (1 l), and saline (1 l), dried over magnesium sulfate and concentrated to give the title compound, CMR (CD$_3$COCD$_3$); 170.0, 161.3, 156.2, 139.8, 123.0, 94.8, 92.2, 80.6, 73.3, 71.8, 69.1, 67.9, 67.2, 55.5, 54.9, 28.4, 21.0, 14.5 δ; MS 613, 501, 459, 413, 369, 333, 287, 225, 153, 140, 127, 98, 69, 57, 41.

EXAMPLE 3

N,N'-Di-t-BOC-2,6-bis(O-formyl)-2'-acetyl-4',5'-didehydrospectinomycin (IV)

N,N'-Di-t-BOC-2,6-bis(O-formyl)-2'-acetylspectinomycin 3'-enolacetate (III, Example 2, 92.08 g), 1,3-dibromo-5,5-dimethyl-hydantoin (20.5 g) and sodium bicarbonate (30 g) are refluxed gently in chloroform (1.6 l) under strong light (e.g. an ordinary incandescent bulb). After 2 hours TLC (ethyl acetate/chloroform, 3/7) showed a slightly less polar, strongly UV active spot. The mixture is diluted with chloroform (1 l), dried over magnesium sulfate and concentrated. The concentrate is chromatographed on silica (875 g) and eluted with chloroform (3 l) and chloroform/ethyl acetate (1/9, 5 l) to give the title compound, CMR (CD$_3$COCD$_3$) 182.4, 173.3, 169.8, 160.9, 156.1, 103.3, 95.6, 93.2, 81.0, 73.0, 72.4, 68.2, 67.5, 67.1, 55.4, 54.8, 30.6, 28.4, 20.9 δ; MS 529, 513, 473, 457, 411, 225, 197, 168, 153, 143, 127, 89, 57, 45.

EXAMPLE 4

N,N'-Di-t-BOC-2'-acetyl-4',5'-didehydro-6'-[(dimethylamino)-methylidene]spectinomycin (V)

N,N'-Di-t-BOC-2,6-bis(O-formyl)-2'-acetyl-4',5'-didehydrospectinomycin (IV, Example 3, 34.97 g) is refluxed at 55° under a nitrogen atmosphere in a solution of DMF dimethylacetal (240 ml) and DMF (250 ml) for 2 hours. TLC (methanol/chloroform, 1/9) shows a slightly less polar spot. Methanol (240 ml) is added and the mixture is refluxed for 2 hours; a TLC probe shows only a much more polar spot. The reaction is concentrated and reconcentrated from chloroform (2×300 ml) to give the title compound, CMR (CD$_3$COCD$_3$) 180.5, 171.0, 170.0, 156.0, 150.1, 95.6, 95.2, 95.1, 88.8, 79.7, 75.7, 74.5, 73.5, 67.3, 66.3, 60.0, 57.0, 30.8, 28.6, 21.2 δ; MS 628, 58.2, 540, 484, 197, 182, 168, 153, 140, 122, 98, 89, 57, 45.

EXAMPLE 5

N,N'-Di-t-BOC-2'-acetyl-4',5'-didehydro-6'-methylidenespectinomycin (VI)

The enamine (V, Example 4, 35.74 g) is dissolved in a solution of ethyl acetate (300 ml) and methanol (70 ml) and brought to pH of 4 by the addition of 2N methanolic hydrochloric acid. Sodium cyanoborohydride is added in small batches while maintaining the pH at 4. When TLC (methanol/chloroform, 1/9) shows all the enamine (V) is converted to a more polar intemediate, the solution is stirred for 0.5 hour and washed with water (250 ml) and sodium hydroxide (1M, 75 ml). The aqueous layers are back extracted with ethyl acetate (200 ml) and the organic phases combined and dried over magnesium sulfate. m-Chloroperoxybenzoic acid (10.0 g) is added until the intermediate is all converted to a less polar TLC spot. The mixture is washed with saturated sodium bicarbonate (300 ml) which is then backwashed with ethyl acetate (100 ml). The organic phases are combined, dried over magnesium sulfate and concentrated. Chromatography on silica (250 g) with elution by chloroform (1 l) and methanol/chloroform (1.5/98.5, 1) gives the title compound, CMR (CD$_3$COCD$_3$) 184, 170.1, 166.0, 157, 131.1, 125.1, 104.4, 94.0, 79.8, 76.0, 74.5, 68.1, 67.7, 66.2, 60.2, 57.2, 30.8, 28.6, 20.9 δ; MS 613, 537, 429, 195, 140, 89, 55, 45.

EXAMPLE 6

N,N'-Di-t-BOC-2'-acetyl-4',5'-didehydro-6'-(1-propen-3-yl)-spectinomycin (VII)

To a mixture of N,N'-Di-t-BOC-2'-acetyl-4',5'-didehydro-6'-methylidenespectinomycin (VI, Example 5, 1.36 g) and copper (I) bromide (0.92 g) in THF (370 ml) in a flame dried flask under nitrogen atmosphere at −78° is added vinylmagnesium bromide (1M in THF, 64.35 ml). TLC probe (methanol/chloroform, 1/9) shows no starting material, only a spot of equal polarity which charred more slowly with sulfuric acid spray. The reaction is quenched by pouring onto a solution of ethyl acetate (1.2 l) and acetic acid (10 ml) and is washed with water (2×500 ml), saturated sodium bicarbonate (2×500 ml) and saline (3×500 ml). The washes are back extracted sequentially with ethyl acetate (200 ml). The organic phases are combined, dried over magnesium sulfate, and concentrated to give the title compound, CMR (CD$_3$COCD$_3$) 185.7, 178.7, 159.9, 141.6, 136.7, 119.6, 107.3, 99.5, 97.0, 92.9, 79.0. 77.6, 70.8, 69.5, 73.6, 60.5, 37.8, 34.0, 24.1, 2.9 δ; high resolutions MS (with KI theoretical for $C_{29}H_{44}N_2O_{12}K$ is 651.2531) measured 651.2563.

EXAMPLE 7

N,N'-Di-t-BOC-6'-(1-propen-3-yl)spectinomycin (VIII)

To a mixture of lithium tri-sec-butyl-borohydride (1M in THF, 29 ml) in THF (75 ml) in a flame dried flask, under $N_2$ atmosphere, at $-78°$ is slowly added a mixture of N,N'-Di-t-BOC-2'-acetyl-4',5'-didehydro-6'-(1-propen-3-l)spectinomycin (VII, Example 6, 8.92 g) and t-butanol (2.7 ml) in THF (75 ml) over a period of 20 minutes. The reaction is stirred for a further 20 minutes, quenched with a solution of ethyl acetate (300 ml), SSB (300 ml), and acetic acid (3 ml) and then washed with saturated sodium bicarbonate (500 ml) and saline (500 ml). The aqueous layers are back extracted with ethyl acetate (100 ml) and SSB (100 ml). All the organic phases are combined, dried over magnesium sulfate, and concentrated to an oil. The oil is chromatographed on silica gel (150 g) and eluted with 0% methanol/chloroform (300 ml), 1% (500 ml), 2.5% (500 ml), and 5% (500 ml) to give an intermediate. This intermediate is added to a solution of 2-propanol (25 ml), water (5 ml) and triethylamine (5 ml) and stirred for 2 hours. The resulting mixture is concentrated and chromatographed on silica gel (225 g), and eluted with 0% methanol/chloroform (0.5 l), 1% (2 l), 2.5% (2 l) and 5% (1 l). The appropriate fractions are pooled and concentrated to give the title compound, TLC (methanol/chloroform, 5/95) indicates the product is slightly more polar than starting material, CMR ($CD_3COCD_3$) 191.5, 157.0, 138.6, 133.3, 115.2, 97.5, 92.1, 79.6, 75.3, 74.4, 71.1, 66.4, 65.6, 60.2, 57.4, 43.8, 35.1, 29.7, 28.5 δ.

EXAMPLE 8

6'-(1-Propen-3-yl)spectinomycin dihydrochloride (IX)

A mixture of N,N'-di-t-BOC-6'-(1-propen-3-yl)spectinomycin (VIII, Example 7, 4.0 g), in methylene chloride (100 ml) at 0° is saturated with gaseous hydrogen chloride. The reaction is stirred 15 minutes and concentrated. The residue is dissolved in water, frozen, and lyophilized to produce the title compound, CMR ($D_2O$) 140.4, 106.5, 95.3, 93.6, 72.9, 71.2, 63.0, 62.5, 62.0, 61.0, 60.0, 41.134.2, 32.2, 31.8, 30.0 δ; high resolution MS (theoretical for $C_{17}H_{29}N_2O_7$ is 373.1975) measured 373.1967.

EXAMPLE 9

N,N'-Di-t-BOC-2'-acetyl-4',5'-didehydro-6'-[(thiomethyl)methyl]spectinomycin (X)

To a solution of N,N'-di-t-BOC-2'-acetyl-4',5'-didehydro-6'-methylidenespectinomycin (VI, Example 5, 0.70 g), t-butanol (5 ml) and THF (5 ml) at 0° is added methanethiol (0.5 ml) and then potassium t-butoxide (catalytic amount). After 2 hours the reaction contains a very slightly less polar spot by TLC (methanol/chloroform, 5/95). The reaction is diluted with ethyl acetate (50 ml), washed with water (2×20 ml) and saline (2×20 ml), dried over magnesium sulfate and concentrated to give the title compound, CMR ($CD_3COCD_3$) 183.2, 174.2, 170.0, 156.4, 103.3, 96.1, 93.7, 79.7, 75.7, 74.2, 67.6, 66.1, 60.4, 57.2, 35.1, 30.8, 58.5, 20.9, 15.3 δ; MS 633, 533, 477, 461, 417, 251, 197, 184, 153, 140, 122, 89, 73, 57, 45.

EXAMPLE 10

N,N'-di-t-BOC-6'-[(Thiomethyl)methyl]spectinomycin (XI)

To a solution of N,N'-Di-t-BOC-2'-acetyl-4',5'-didehydro-6'-thiomethyl)methyl]spectinomycin (X, Example 9, 0.30 g), t-butanol (1.89 ml), and THF (6 ml) in a flame dried flask, under nitrogen atmosphere, at $-78°$ is added lithium tri-sec-butyl borohydride (1M in THF, 0.96 ml). After 20 minutes the reaction is quenched with a solution of ethyl acetate (20 ml), SSB (20 ml) and acetic acid (0.10 ml), washed with saturated sodium bicarbonate (2×30 ml) and saline (2×20 ml), dried over magnesium sulfate, and concentrated to an oil. To this is added 2-propanol (7 ml), water (0.1 ml) and triethylamine (0.1 ml). The mixture is stirred for 2.5 hours and concentrated to a solid. The solid is chromatographed on silica gel (10 g) and eluted with 0% methanol/chloroform (100 ml), 1% (200 ml), 2.5% (200 ml) and 5% (100 ml). The appropriate fractions are pooled and concentrated to give the title compound, CMR ($CD_3COCD_3$) 190.0, 159.0, 100.5, 95.0, 82.7, 82.2, 78.0, 77.2, 73.3, 69.0, 63.0, 46.8, 38.4, 33.0, 31.5, 11.1, 3.0 δ; MS (with KI, theoretical for $C_{26}H_{44}N_2O_{11}SK$ is 6.31.2303); measured 631.2347.

EXAMPLE 11

6'-[(Thiomethyl)methyl]spectinomycin dihydrochloride (XII)

A solution of N,N'-di-t-BOC-6'-[(thiomethyl)methyl]spectinomycin (XI, Example 10, 0.10 g) in methylene chloride (15 ml) at 0° is saturated with hydrogen chloride gas. After 15 minutes the solution is concentrated and the residue is dissolved in water (25 ml), frozen, and lyophilized to give the title compound, CMR ($D_2O$); 94.0, 92.3, 71.9, 70.1, 66.3, 66.0, 62.0, 60.0, 59.0, 39.8, 33.8, 31.1, 30.6, 29.2, 14.6 δ; MS (theoretical for $C_{16}H_{29}N_2O_7S$ is 393.1695); measured 393.1677.

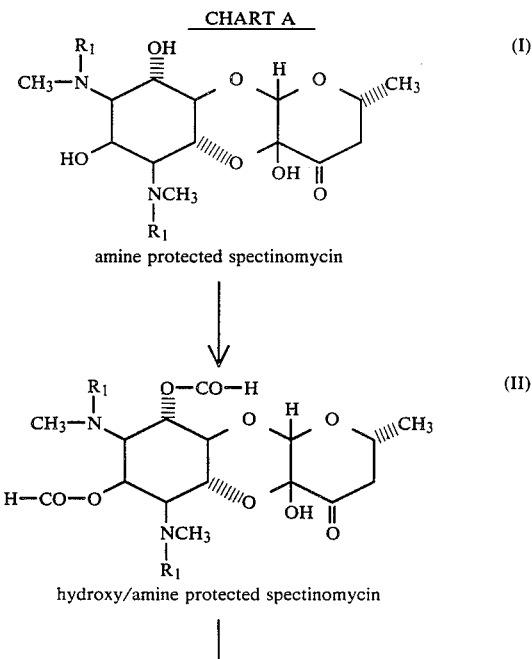

CHART A (I) amine protected spectinomycin (II) hydroxy/amine protected spectinomycin

-continued
CHART A
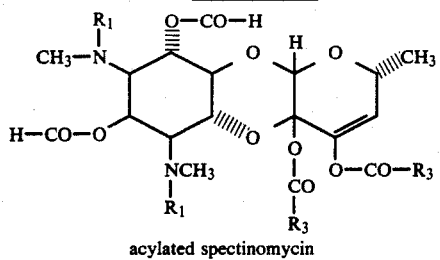
acylated spectinomycin
CHART B
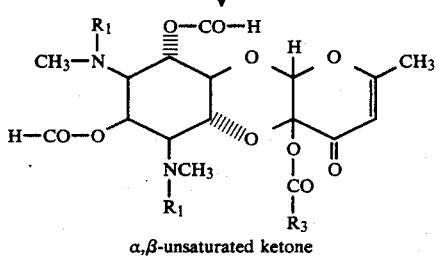
α,β-unsaturated ketone
triprotected 6'-alkenyl-4',5'-didehydro-spectinomycin
amine protected 6'-alkenyl-spectinomycin
-continued
CHART B
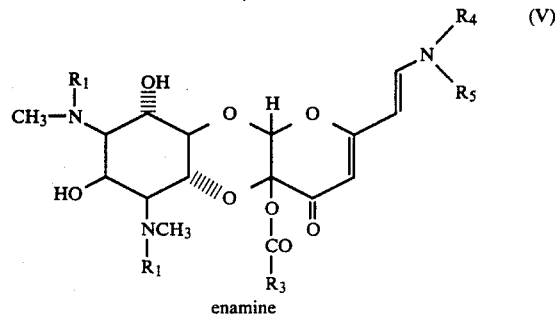
enamine
6'-methylidene substituted spectinomycin
CHART C
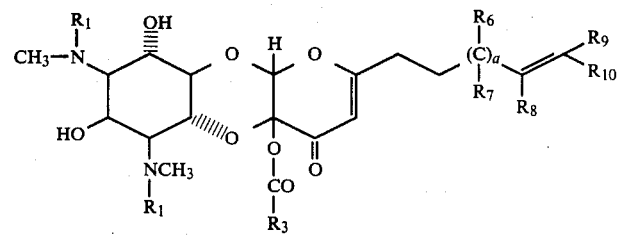
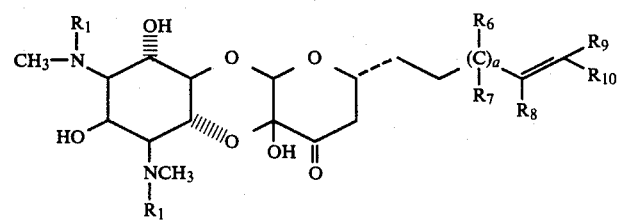
(III)
(IV)
(V)
(VI)
(VII)
(VIII)

6'-alkenyl-spectinomycin

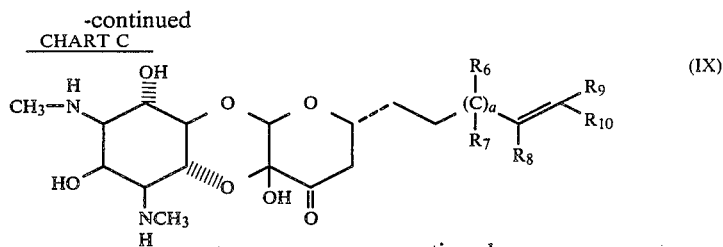

-continued
CHART E
6'-thiomethyl substituted compound

CHART D

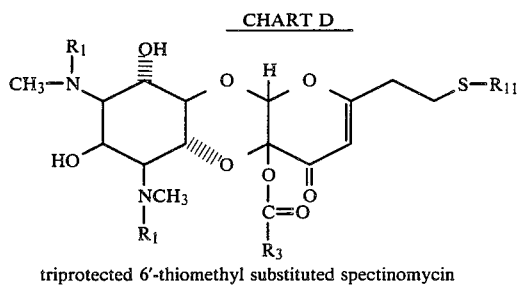

triprotected 6'-thiomethyl substituted spectinomycin

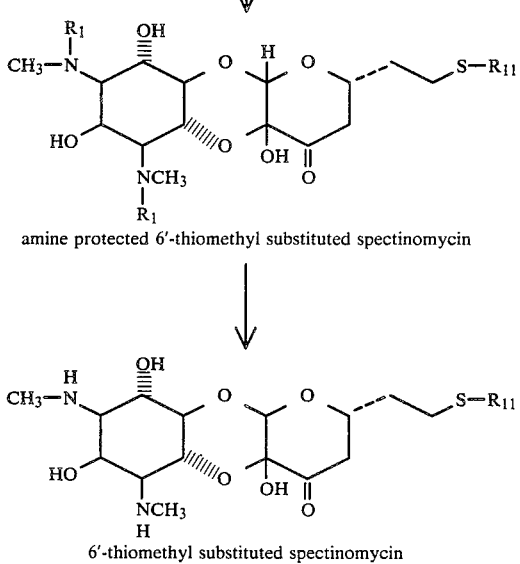

amine protected 6'-thiomethyl substituted spectinomycin

6'-thiomethyl substituted spectinomycin

CHART E

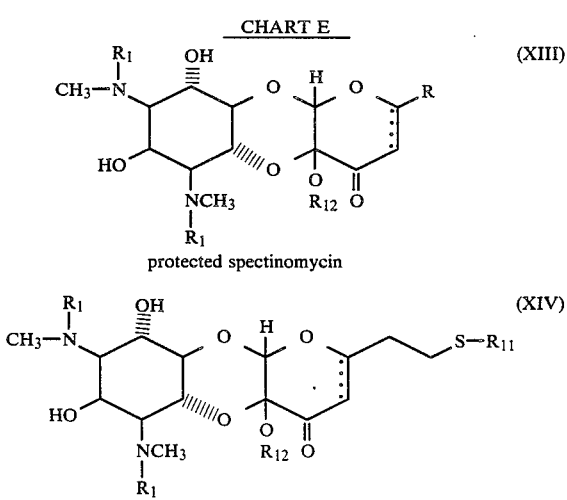

protected spectinomycin

I claim:

1. A 6'-thiomethyl-substituted spectinomycin of the formula

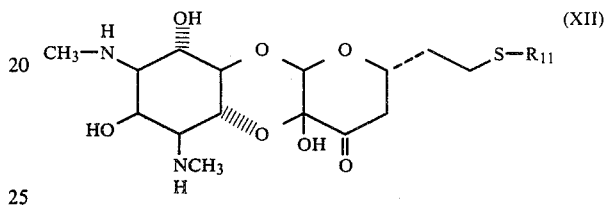

where $R_{11}$ is $C_1$-$C_5$ alkyl, —$CH_2$—($C_2$-$C_4$ alkenyl), $C_5$-$C_8$ cycloalkyl, phenyl or phenyl substituted with 1 through 5 —F, —Cl, —Br, or —I and pharmaceutically acceptable salts thereof.

2. A 6'-thiomethyl-substituted spectinomycin according to claim 1 where $R_{11}$ is $C_1$-$C_3$ alkyl.

3. A 6'-thiomethyl-substituted spectinomycin according to claim 1 which is 6'-[(methylthio)methyl]spectinomycin.

4. A 6'-thiomethyl-substituted compound of the formula (XIV)

where
$R_1$ is —COO—(t-butyl), —COO—$CH_2CH_2$—Si($CH_3$)$_3$ or —COO—$CH_2CH_2Cl$;
$R_3$ is $C_1$-$C_8$ alkyl;
$R_{11}$ is $C_1$-$C_3$ alkyl, $C_5$-$C_8$ cycloalkyl or phenyl;
$R_{12}$ is —H or $R_3$—CO—;
⋯ is a single or double bond with the proviso that
(1) when ⋯ is a double bond, $R_{12}$ is $R_3$—CO— and
(2) when ⋯ is a single bond, $R_{12}$ is a hydrogen atom.

5. A 6'-thiomethyl-substituted compound according to claim 4 where $R_1$ is —COO—(t-butyl).

6. A 6'-thiomethyl-substituted compound according to claim 4 where $R_3$ is a methyl group.

7. A 6'-thiomethyl-substituted compound according to claim 4 where $R_{11}$ is $C_1$-$C_3$ alkyl.

8. A 6'-thiomethyl-substituted compound according to claim 4 where ⋯ is a double bond.

9. A 6'-thiomethyl-substituted compound according to claim 4 where ⋯ is a single bond.

* * * * *

UNITED STATES PATENT OFFICE
CERTIFICATE OF CORRECTION

Patent No. 4,730,059          Dated 8 March 1988

Inventor(s) David R. White

It is certified that error appears in the above-identified patent and that said Letters Patent are hereby corrected as shown below:

Column 2, line 45: "$(R_g)$" should read --$(R_9)$--.
Column 3, line 18: "XII" should read --XIII--.
Column 4, line 10: "......" should read --.....--.
Column 4, line 13: "..." should read --.....--.
Column 4, line 22: "or" should read --of--.
Column 4, line 24: "$C_s-C_y$" should read --$C_x-C_y$--.
Column 5, line 9: "N,N'-d-t-" should read --N,N'-Di-t- --.
Column 6, line 6: "34.97 g" should read --34.07 g--.
Column 7, line 12: "3-1" should read --3-yl--.
Column 8, line 24: "63.0, 46.8, 38.4," should read --63.0, 60.0, 46.8, 38.4,--.
Column 8, line 26: "6.31.2303" should read --631.2303--.
Column 10 (Chart C) (VIII): " 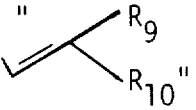 should read -- 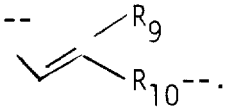 --.

Column 12 (Chart C) (IX): " 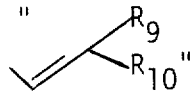 should read -- 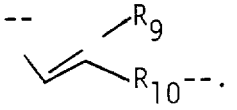 --.

Column 12, lines 66 & 68: "where     is" should read --where .... is--; and "where     is" should read --where .... is--.

Signed and Sealed this

Twenty-seventh Day of September, 1988

Attest:

DONALD J. QUIGG

Attesting Officer          Commissioner of Patents and Trademarks